(12) United States Patent
Glaug

(10) Patent No.: US 6,514,233 B1
(45) Date of Patent: Feb. 4, 2003

(54) EFFICIENTLY MANUFACTURABLE ABSORBENT DISPOSABLE ARTICLES, SUCH AS ADULT BRIEFS AND CHILD DIAPERS, AND METHOD OF MANUFACTURING PLURAL SUCH ARTICLES

(75) Inventor: Frank S. Glaug, Chester Springs, PA (US)

(73) Assignee: Tyco Healthcare Retail Services AG (CH)

(*) Notice: Subject to any disclaimer, the term of this patent is extended or adjusted under 35 U.S.C. 154(b) by 3 days.

(21) Appl. No.: 09/668,189

(22) Filed: Sep. 22, 2000

(51) Int. Cl.[7] .................................................. A61F 13/15

(52) U.S. Cl. .................. 604/385.25; 604/389; 604/391; 604/393

(58) Field of Search ........................... 604/378, 385.01, 604/385.24, 385.28, 389, 391, 392, 396, 393

(56) References Cited

U.S. PATENT DOCUMENTS

| | | | |
|---|---|---|---|
| 4,738,675 A | | 4/1988 | Buckley et al. |
| 4,753,646 A | * | 6/1988 | Enloe .......................... 604/378 |
| 4,764,234 A | | 8/1988 | Smits et al. |
| 4,764,242 A | | 8/1988 | Gressick et al. |
| 4,795,451 A | | 1/1989 | Buckley |
| 4,804,379 A | | 2/1989 | Toth et al. |

(List continued on next page.)

FOREIGN PATENT DOCUMENTS

| | | |
|---|---|---|
| EP | 0 797 970 A2 | 1/1997 |
| EP | 0 768 073 A1 | 4/1997 |
| WO | WO 00/30584 | 6/2000 |
| WO | WO 00/37010 | 6/2000 |

OTHER PUBLICATIONS

International Search Report for PCT/US01/25984.

*Primary Examiner*—Dennis Ruhl
*Assistant Examiner*—Jamisue Webb
(74) *Attorney, Agent, or Firm*—Caesar, Rivise, Bernstein, Cohen & Pokotilow, Ltd.

(57) ABSTRACT

A disposable absorbent article, e.g., a diaper, and a method of manufacturing plural such articles. Each diaper includes a front section, a rear section and an intermediate section. Each section is a generally planar member formed of a flexible material having a top edge, a bottom edge and an opposed pair of side edges. The bottom edge of the front section is somewhat concave, and the bottom edge of the rear section is somewhat convex. The intermediate section is formed of a fluid pervious cover-stock, a fluid impervious barrier layer, and an absorbent core interposed therebetween. The intermediate section is of generally rectangular shape having a pair of elasticized sides and an pair of end portion one of which is adhesively secured to the middle of the front section, while the other end portion is similarly secured to the middle of the rear section. The front and rear sections are arranged to be releasably secured to each other by fastening tapes to mount the diaper. A portion of the bottom edge of the front section, one side of the intermediate section and a corresponding portion of the bottom edge of the rear section form one leg hole of the diaper. Corresponding portions of the front, rear and intermediate sections form the other leg hole. The tensioned intermediate section forms a pair of upstanding walls conforming to the crotch of the wearer to prevent leakage from the diaper. The diapers are made by providing plural sheet units, each making up a front section of one diaper and a rear section of the next succeeding diaper. Those units are adhesively secured to respective ends of an intermediate section in a sequential line of such sections. Then the two sheet units that are secured to the intermediate section are each severed transversely to complete a diaper. This process is repeated for succeeding diapers.

22 Claims, 7 Drawing Sheets

U.S. PATENT DOCUMENTS

| | | | |
|---|---|---|---|
| 4,900,318 A | | 2/1990 | Toth |
| 4,940,464 A | * | 7/1990 | Van Gompel et al. .. 604/385.22 |
| 5,071,415 A | | 12/1991 | Takemoto |
| 5,263,948 A | | 11/1993 | Karami et al. |
| 5,263,949 A | | 11/1993 | Karami et al. |
| 5,308,344 A | | 5/1994 | Toth |
| 5,439,459 A | | 8/1995 | Tanji et al. |
| 5,599,334 A | | 2/1997 | Johnston et al. |
| 5,628,741 A | | 5/1997 | Buell et al. |
| 5,643,243 A | | 7/1997 | Klemp |
| 5,643,377 A | | 7/1997 | Juergens |
| 5,649,919 A | | 7/1997 | Roessler et al. |
| 5,776,121 A | | 7/1998 | Roe et al. |
| 5,782,819 A | * | 7/1998 | Tanzer et al. .................. 2/337 |
| 5,904,675 A | | 5/1999 | Laux et al. |
| 5,906,603 A | | 5/1999 | Roe et al. |
| 6,010,586 A | | 1/2000 | Suprise |
| 6,217,563 B1 | * | 4/2001 | Van Gompel et al. ...... 604/378 |
| 6,312,420 B1 | * | 11/2001 | Sasaki et al. .......... 604/385.01 |

\* cited by examiner

\* cited by examiner

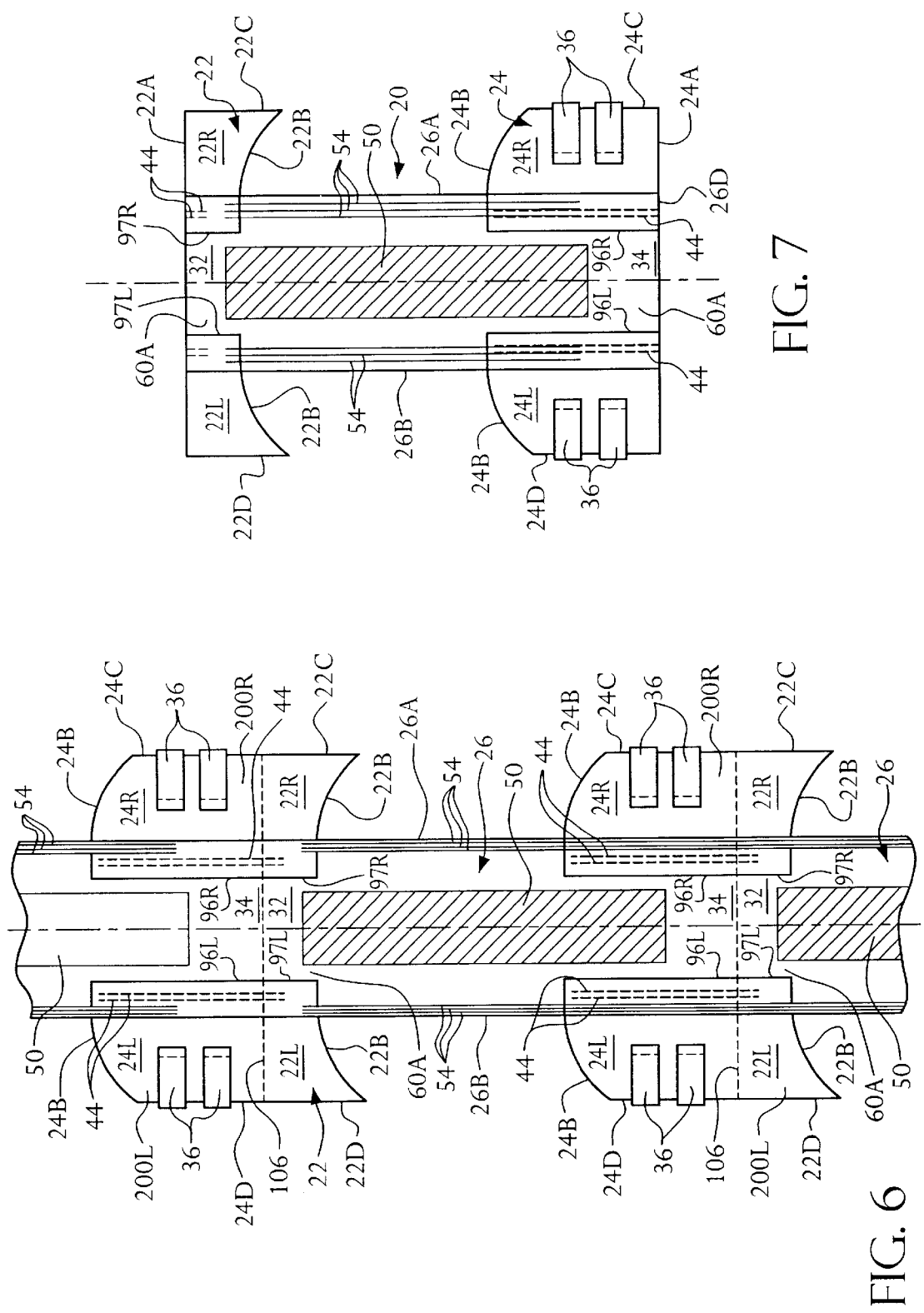

EFFICIENTLY MANUFACTURABLE ABSORBENT DISPOSABLE ARTICLES, SUCH AS ADULT BRIEFS AND CHILD DIAPERS, AND METHOD OF MANUFACTURING PLURAL SUCH ARTICLES

FIELD OF THE INVENTION

This invention relates generally to disposable absorbent articles, e.g., diapers for children/infants and briefs for adults, and more specifically to articles of that type which are can be manufactured very efficiently and economically and which exhibit good protection from leakage, good fit and comfort.

BACKGROUND OF THE INVENTION

Disposable absorbent articles, such as infant/child diapers and adult incontinent briefs, are designed to absorb and contain body waste, e.g., urine and/or feces, to prevent such waste from soiling, wetting, or otherwise contaminating clothing or other articles, such as bedding, that come in contact with the wearer. Many such diapers/briefs are commercially available. Moreover, the patent literature is replete with examples of various diaper/brief constructions and methods of manufacturing them.

For example, In U.S. Pat. No. 4,764,234 (Smits, et al.), which is assigned to the same assignee as this invention and whose disclosure is incorporated by reference herein, there is disclosed a method of manufacturing an absorbent pad for utilization as a diaper or an adult incontinent brief. The method entails providing a moving web of material forming sequential backing sheets for the article. Nozzles are utilized to apply a pair of continuous bands of adhesive to the back sheet of the pad, prior to its assembly. The nozzles eject the adhesive onto a moving web which makes up the backing sheet and are shifted sideways during their extrusion of adhesive from a first location to a second location. This action generates a pair of non-linear bands of adhesive on the backing sheet. The nozzles are again shifted from their second location to their original first location. The elastic band is not shifted when the nozzles are, thus effectuating securement of the elastic bands only on the portions of the backing sheets where the adhesive was applied at the first location. The sequentially located sheets are cut on opposite marginal side to form leg cut-out areas, whereupon only those portions of the elastic bands at the center of each of the leg cut-out areas contract to form a gather thereat.

U.S. Pat. No. 4,764,242 (Gressick et al.), which is also assigned to the same assignee as this invention and whose disclosure is also incorporated by reference herein, discloses a machine for manufacturing a diaper or brief like that disclosed in the aforementioned Smits et al. patent.

U.S. Pat. No. 4,795,451 (Buckley), which is also assigned to the same assignee as this invention and whose disclosure is also incorporated by reference herein, discloses a disposable absorbent pad for use as a baby diaper or an adult incontinent brief wherein the backing sheet of the diaper has a pair of continuous bands of adhesive arranged in a stepped generally longitudinal configuration thereon. An elastic band is disposed over the mid-portion of the adhesive being stepped to the side, out of contact with the elastic. When the pads are cut in the assembly process, only that portion of elastic in contact with the adhesive causes the pad to gather. The remaining end portions of the adhesive bands are secured to the intermediate layer of absorbent fluff material, helping it remain in place, and act as a fluid barrier on the sides of the absorbent pad.

U.S. Pat. No. 4,804,379 (Toth et al.), which is also assigned to the same assignee as this invention and whose disclosure is also incorporated by reference herein, discloses a disposable absorbent pad for utilization as a diaper or adult brief. The pad is an absorbent member covered on one side by a sheet of fluid impervious material, and on the other side by a pair of generally parallel strips of fluid impervious material overlapping the absorbent pad and the backing sheet, in the crotch area to prevent leakage of fluid from the absorbent pad in the crotch area. The pad includes a pair of opposed leg cut-outs each of which is elasticized by a linear elastic band.

In U.S. Pat. No. 5,439,459 (Tanji et al.), there is disclosed an arrangement of a disposable diaper in which there are provided elastic members extending not only along opposite side edges of an opening formed in a skin-contacting topsheet but also further extending beyond longitudinally opposite ends of the opening substantially to longitudinally opposite ends of the skin-contacting topsheet so that the opening may sufficiently rise up together with the skin-contacting topsheet to assure reliable introduction of excretions through this opening into a pocket space defined between the skin-contacting topsheet and a separately provided topsheet underlying the skin-contacting topsheet.

In U.S. Pat. No. 5,628,741 (Buell et al.), there is disclosed absorbent articles having an elastomeric member and an associated non-elastic web for improving the dynamic fit as well as containment characteristics. A portion of the non-elastic web coincides with at least a portion of the elastomeric member. The portion of the nonelastic web is mechanically prestrained to improve not only the extension of the elastomeric member, but also the heat-shrink contraction of preferred elastomeric members.

In U.S. Pat. No. 5,643,243 (Klemp), there is disclosed a disposable diaper having opposed leg cut-outs and unitary elasticized leg cuffs disposed on the interior surface of the diaper along the leg cut-outs.

In U.S. Pat. No. 5,643,377 (Juergens), there is disclosed a process for making a wearable, absorbent article wherein two longitudinally extending barrier leg cuffs are attached to a chassis and the barrier leg cuffs are joined to the article so that they are directed inwardly toward a longitudinally extending centerline in the first waist region of the article and directed outwardly away from the longitudinally extending centerline in the second waist region of the article. The article is made by a method that entails first attaching the cuffs in the first waist region and then in the second waist region in one embodiment and, in another embodiment, being attached in the second waist region first and then in the first waist region of the article. The method also entails attaching the barrier leg cuffs to the article outboard of the longitudinally extending centerline in both the first waist and second waist regions of the article and wherein the barrier leg cuffs are joined partially to the article in the crotch region.

In U.S. Pat. No. 5,649,919 (Roessler et al.), there is disclosed an absorbent article which has a lateral width, a longitudinal length, longitudinally extending side margins, a front waistband portion, a back waistband portion, and an intermediate portion which interconnects the front and back waistband portions. The article comprises a backsheet layer and an absorbent retention portion superposed on the backsheet layer. A liquid permeable topsheet layer is superposed on the retention portion to sandwich the retention portion between the topsheet layer and the backsheet layer. An elasticizing means form elasticized gathers at leg opening portions of the article. The elasticizing means include a front set of laterally opposed, longitudinally extending leg elastic members located in the article side margins in at least the intermediate portion of the article. The front elastic members are arranged asymmetrically with respect to the article length and have a selected offset toward the front waistband portion of the article. A back set of laterally opposed, longitudinally extending leg elastic members are constructed separate from the front set of elastic members and are located in the article side margins in at least the intermediate portion of the article. The back elastic members are arranged asymmetrically with respect to the article length and have a selected offset toward the back waistband portion of the article.

In U.S. Pat. No. 5,776,121 (Roe et al.), there is disclosed absorbent articles, such as disposable diapers, having two waist regions and a crotch region. The absorbent articles comprise a liquid pervious topsheet, a liquid impervious backsheet, an absorbent core disposed between the topsheet and the backsheet, and a pair of longitudinally extending barrier cuffs. The barrier cuffs are formed from a lateral extension of the topsheet and the backsheet in at least the crotch region of the absorbent article using material that is normally discarded when the crotch area is formed. A cuff area is defined by pairs of laterally opposed cuts in the lateral extension of the topsheet and the backsheet. The cuff area is then folded and joined to the topsheet or other underlying structure to form the barrier cuff and an optional gasketing cuff.

In U.S. Pat. No. 5,904,675 (Laux et al.), there is disclosed an absorbent article has a longitudinal length dimension, a lateral cross dimension, a front waistband portion, a back waistband portion and an intermediate portion which interconnects the front and back waistband portions. The article includes a backsheet layer having a pair of laterally opposed side margins, with each side margin having an outwardly concave, terminal side edge contour located at appointed leg opening regions in an intermediate portion of each of the side margins. Each concave side edge contour has a selected longitudinal extent along the length dimension of the article. A liquid permeable topsheet layer is connected in superposed relation to the backsheet layer, and an absorbent body is sandwiched between the topsheet layer and the backsheet layer. A separate, elasticized and gathered leg gusset is connected to the article along each of the appointed leg opening regions, and each leg gusset is configured to extend beyond and to bridge between opposed, spaced-apart portions of an associated one of the concave side edge contours of the backsheet layer.

In U.S. Pat. No. 5,906,603 (Roe et al.), there is disclosed a disposable absorbent article including a topsheet, a backsheet, and an absorbent core having a pair of opposed longitudinal edges. The absorbent article includes a leg cuff extending at least laterally outwardly from each opposed longitudinal edge. Each leg cuff has a proximal edge, a distal edge and an elasticized region disposed between the proximal edge and the distal edge. The elasticized region has an inner edge, an outer edge and a width. The proximal edge of each leg cuff extends generally longitudinally along and adjacent to at least a portion of one of the opposed longitudinal edges and the distal edge of each of said leg cuffs is disposed laterally outwardly from the proximal edge. Each leg cuff includes an inner bond disposed adjacent at least a portion of the proximal edge of each leg cuff. An outer bond is spaced laterally outwardly from the inner bond, the spacing between the inner bond and said outer bond defining a leg cuff base width. Each leg cuff also includes an inner wall that extends upwardly and laterally outwardly from the inner bond to the inner edge of the elasticized region having a first height, and an outer wall that extends upwardly and laterally inwardly from the outer bond to the outer edge of the elasticized region having a second height. An elastic element is disposed in the elasticized region of each leg cuff and is provided generally parallel to the wearer's skin.

In U.S. Pat. No. 6,010,586 (Suprise), there is disclosed a disposable absorbent article which defines a first side portion, a second side portion, and a longitudinal centerline between the side portions. The absorbent article comprises an outer cover and an absorbent insert which is connected to the outer cover. The outer cover comprises a first side panel which is located in the first side portion of the absorbent article and a second side panel which is located in the second side portion of the absorbent article. An edge of the first side panel is connected to an edge of the second side panel to provide a seam which extends along the longitudinal centerline between the side portions of the absorbent article. The opposite waist regions on each side panel are configured to encircle the legs of the wearer and releasably engage together about the hips of the wearer. The disposable absorbent article has an aesthetically pleasing garment-like appearance and is readily refastenable about the hips of the wearer.

While the prior art disposable absorbent diapers and briefs may be generally suitable for their intended purposes, they still leave much to be desired from the standpoints simplicity of construction and of ease and economy of manufacture. For example, some of the aforementioned patents require cutting away portions of the article to form the leg cut-outs or openings. This can be a somewhat complex undertaking and is also wasteful of materials and resources, e.g., the cut away material is scrap which must be removed and discarded (all of which likely result in higher production costs). Moreover, in order to ensure that there will be no leakage around the leg openings, such openings are typically gathered by use of elastic materials, e.g., threads or beads, applied thereto. or standing leg cuffs or other upstanding elasticized wall-like barriers can be provided. Either of these approaches can also present a somewhat complex, and production-cost-increasing undertaking. While eliminating elasticized leg openings would inherently lower the production cost of the diaper, it would likely result in the increased tendency of the diaper/brief to leak, while also be ill-fitting. Moreover, such a device would likely be somewhat uncomfortable due to its lack of a close conforming fit to the wearer's anatomy. Thus, a need presently exists for a diaper/adult brief that is simple in construction, can be manufactured economically and efficiently without wastage, and which provides a good fit, resistance to leakage and wearing comfort. It is to those ends that this invention is directed.

SUMMARY OF THE INVENTION

A disposable absorbent article, e.g., a diaper or an adult brief, arranged to be worn by a wearer to trap and collect waste materials and a method of economically manufacturing the article.

The article basically comprises a front section, a rear section and an intermediate section. The front section, e.g., either one or two mirror-image panels, is a generally planar member formed of a flexible material, e.g., a non-woven material, a non-woven material and a poly-film adhesively secured together, a poly-laminate, a poly-film, etc. The panel(s) of the front section has(have) a top edge, a somewhat concave bottom edge and an opposed pair of side edges. The rear section is preferably formed of the same material as the front section and may also be a single panel or a pair of mirror-image panels that have(has) a top edge, a somewhat convex bottom edge and an opposed pair of side edges, said intermediate section being an elongated member formed of a flexible material having a pair of side edges and an pair of end edges.

The intermediate section is an elongated member formed of a flexible material, e.g., a moisture pervious cover-stock layer, a moisture barrier layer and an absorbent core interposed therebetween. The intermediate section may optionally include a fluid transfer layer interposed between the cover-stock layer and the core. In any case the intermediate section includes a pair of elongated side edges and an pair of end edges.

The intermediate section is fixedly, e.g., adhesively, secured to said front section intermediate the front section side edges adjacent one of the intermediate section's end edges. The other end of the intermediate section is similarly fixedly secured to the rear section intermediate the rear section's side edges.

The front and rear sections are arranged to be releasably secured to each other to mount the article on the wearer, with a first portion of the concave bottom edge of the front section adjacent one side edge of the front section, one side edge of the intermediate section, and a first portion of the convex arcuate bottom edge of the rear section adjacent the one side of the front section forming one leg hole for accommodating one leg of the wearer. In a similar manner a second portion of the concave bottom edge of the front section adjacent the other side edge of the front section, the other side edge of the intermediate section, and a second portion of the convex arcuate bottom edge of the rear section adjacent the second side of the front section forms the other leg hole for accommodating the other leg of the wearer.

The intermediate section is elasticized, e.g., includes tensioned elastic threads extending along the respective sides of the intermediate section to form to a pair of upstanding walls conforming to the crotch of the wearer. The intermediate section is arranged to absorb and trap waste material therein, and may optionally include a pair of standing leg gathers or cuffs for additional protection from leakage of waste materials out of the crotch area.

To facilitate the releasable mounting of the article on the wearer the article includes at least two fastening members, one on each side of one of the article's sections, e.g., the rear section. The fastening members may be adhesive tapes or multi-hook tabs. In addition the front panel may include landing zones, e.g., (BOPP) Bi-axially orientated Polypropylene film or a multi-loop or plush material to be releasably engaged by fastening tapes or multi-hook tabs.

The method aspect of this invention entails manufacturing plural disposable absorbent articles like those described above. The method basically comprising the steps of providing a series of sheet units along an assembly feed line. Each of the sheet units comprises an area forming the front section of a leading article, e.g., diaper, to be manufactured and the rear section of the next succeeding article to be manufactured. The front and rear sections of each of the sheet units merge together at an interface line. Each interface line forms the top edge of respective ones of the front and rear sections of the articles being manufactured.

A series of said intermediate sections are also provided along another assembly feed line. Each of the intermediate sections has a leading end portion and a trailing end portion and a pair of long sides along which respective tensioned elastic lines are provided.

The method further entails conveying a first one of the sheet units into engagement with the leading end portion of a first intermediate section of the series of intermediate sections and fixedly securing, e.g., adhesively securing, the sheet unit thereto. A second one of the sheet units is conveyed into engagement with the trailing end portion of the first intermediate section of the series of intermediate sections and fixedly secured, e.g., adhesively bonded, thereto. Then the interface lines of the first and second sheet units are severed therealong to form one of the articles and to separate it from the assembly line.

In accordance with one preferred embodiment of the invention the area of each unit defining the front section of the article and the area of that unit defining the rear section of the article are of complementary shape.

DESCRIPTION OF THE DRAWING

FIG. 6 is a top plan view, similar to FIG. 4, but showing the comparable step in a continuous manufacturing process for assembling the front and rear sections to the intermediate section of alternative embodiment of the absorbent article, e.g., diaper, shown in FIG. 1, and wherein the front and rear sections of each article are each of a "two-piece" or split-panel construction;

FIG. 7 is a top plan view, similar to FIG. 5, but showing the comparable later step in the manufacturing process shown in FIG. 6, but after severing of one of the completed articles from the manufacturing line;

DETAILED DESCRIPTION OF THE PREFERRED EMBODIMENT

Figure 1:
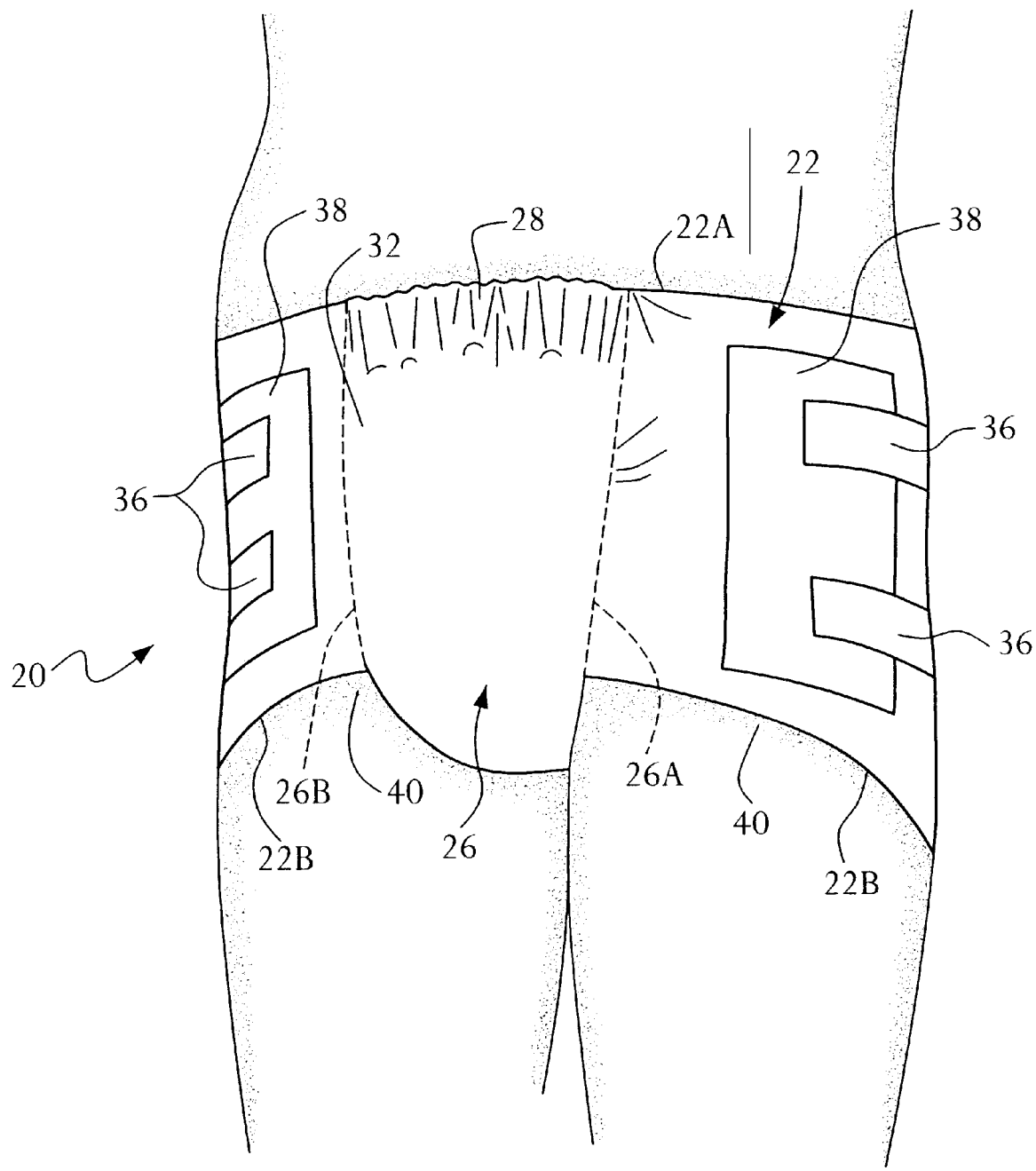
FIG. 1 is an isometric view of a preferred embodiment of one type of disposable absorbent article, e.g., a diaper, having a front section, a rear section, and an intermediate section constructed in accordance with this invention and shown in place on a child with the front section and rear section connected together along their respective sides, and with the intermediate section forming the crotch of the article.
Figure 2:
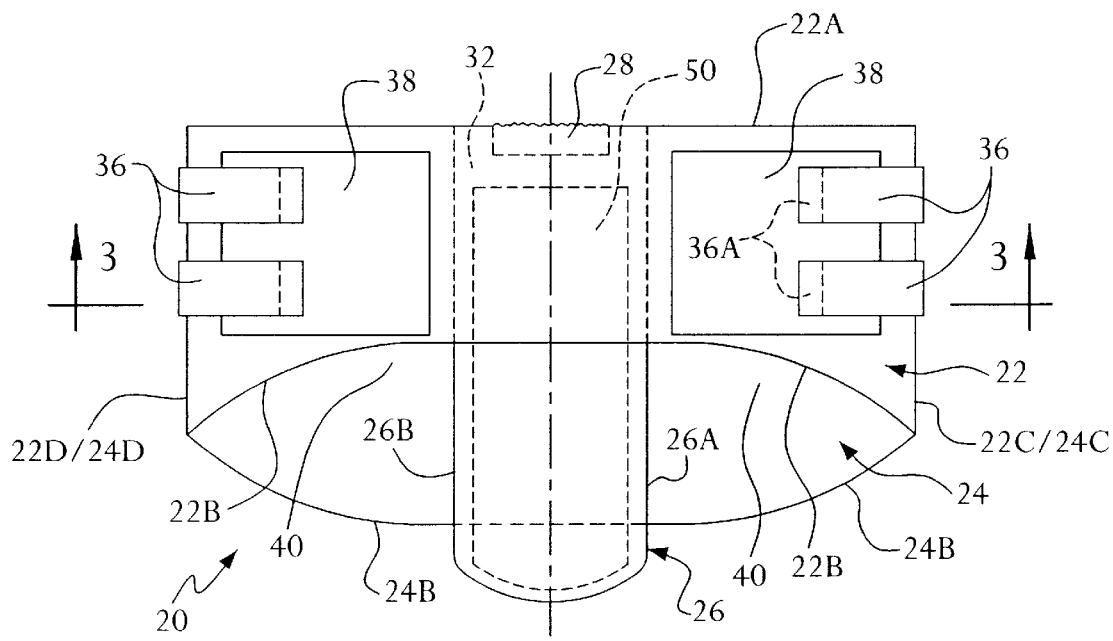
FIG. 2 is a reduced front plan view of the absorbent article of FIG. 1, shown with the front section and rear section having been connected together.

Referring now to the various figures of the drawing wherein like reference characters refer to like parts, there is shown in FIGS. 1 and 2 a disposable absorbent article 20 constructed in accordance with one embodiment of this invention. The article 20 of FIG. 1 is in the form of a child's diaper comprising a front portion or section 22, a back portion or section 24 (FIG. 2), and an intermediate section 26 forming the crotch portion of the diaper. The front section includes an elastic area 28 formed by elastic threads (to be described later). The rear section also includes an elastic area 30 (FIGS. 4–5) similarly formed. Although the article 20 is illustrated and described as a diaper, the present invention can be utilized in other similar types of absorbent disposable articles, e.g., adult incontinence briefs. It should be pointed out that as used herein the term "disposable" means that article is designed to be used until soiled, either by urination or otherwise, and then discarded, rather than being washed and used again.

The details of the three sections 22, 24 and 26 of the diaper 20 will be described in detail later. Suffice it for now to state that owing to their shape, construction and arrangement, they are arranged to be fabricated and assembled on a continuous basis into diapers or adult briefs more economically than the prior art, while offering the same level of protection from leakage and without any sacrifice in comfort or fit. In fact, the diapers/briefs of this invention are likely to prove more comfortable than prior art devices, particularly when the wearer is sitting down.

As best seen in FIGS. 1, 2 and 4–7, the diaper's front section 22 is of somewhat different shape than the rear section 24, although as will be described later they are of complementary shape to be die cut from a sheet or web of material without any wastage. In particular the front section 22 is a generally planar panel (although it may be two mirror image panels as will be described later) that includes a generally linear top edge 22A, a generally concave arcuate bottom edge 22B, and an opposed pair of linear side edges 22C and 22D (FIGS. 4–7). The rear section 24 is also a generally planar panel (although it may also be two mirror image panels as will be described later), formed of the same material(s) as the front panel(s), but having a a generally linear top edge 24A (FIGS. 5 & 7), a generally convex arcuate bottom edge 24B (FIGS. 2 and 4–7), and an opposed pair of linear side edges 24C and 24D (FIGS. 4–7). As will be described later, the front and rear sections can be constructed of various materials in various configurations and arrangements.

The details of the intermediate section 26 forming the crotch portion of the diaper 20 will also be described later (there are also various embodiments of that section). Suffice it for now to state that the intermediate section 26 is an elongated member that includes an opposed pair of end regions 32 and 34 (FIGS. 1, 2 and 4–7), which are fixedly secured to the inner surface of the front and rear sections 22 and 24, respectively. The intermediate section 26 is in the form of a generally planar member which is elasticized (as will be described later) to enable it to form a somewhat cup-shaped or bucket-shaped member having a pair of upstanding walls to conform to the crotch of the wearer between the wearer's legs. The intermediate section 26 includes a pair of long, linear sides 26A and 26B, and a pair of short linear end edges 26C and 26D (FIGS. 1, 2 and 4–7).

The side edge 24C of the rear section 24 is arranged to be releasably secured by means of at least one and preferably two fastening tapes 36, e.g., an adhesive tape or a multi-hook fastening tape, to a portion of the front section panel 22 adjacent the side edge 22C. In a similar manner the side edge 24D of the rear section 24 is arranged to be releasably secured by means of at least one and preferably two similar fastening tapes to a portion of the front section 22 adjacent the side edge 22D. Depending upon the material(s) forming the front section 22 and the construction of the fastening tapes 36, the front section may include at least one, and preferably two "landing zones" 38 (FIGS. 1 and 2) whose details will be described later. Suffice for now to state that the landing zones provide areas on the front panel to which the fastening tapes 36 may be releasably secured repeatedly to enable the wearer to achieve a good fit and to enable the diaper brief to be put on and taken off as many times as desired.

As best seen in FIGS. 2 and 4–7, the height of the rear section 24 is substantially greater than the height of the front section 22, i.e., the distance between the central portion of the bottom edge 24B of the rear section and the central portion of the linear top edge 24A of the rear section is substantially greater than the distance between the central portion of the bottom edge 22B of the front section and the central portion of the linear top edge 22A of the front section. Accordingly, as can be readily seen in FIGS. 1 and 2, when the diaper 20 is mounted and secured in place on the wearer, the concave arcuate portion of the bottom edge 22B of the front panel 22 adjacent the side 22C, the contiguous side edge 26A of the intermediate section 26, and the contiguous convex arcuate portion of the bottom edge 24B of the rear panel adjacent the side 24C form one leg hole or opening 40 for the wearer. In a similar manner the concave arcuate portion of the bottom edge 22B of the front panel 22 adjacent the side 22D, the contiguous side edge 26B of the intermediate section 26, and the contiguous convex arcuate portion of the bottom edge 24B of the rear panel adjacent the side 24D form the other leg hole or opening 40 for the wearer.

As should be readily apparent to those skilled in the art from the foregoing the front and rear sections of the diaper are of very efficient design from an ergonomic standpoint in the interests of fit and comfort. In this regard the fact that the rear section extends substantially below the front section ensures extra coverage of the lower buttocks area of the wearer. The high leg opening portions at the front section (the portions of the leg opening 40 at the intersection of the bottom edge 22B of the front section and the contiguous portions of the intermediate section 26 that is located at the wearer's upper groin/thigh area) ensures that the diaper is very comfortable to wear irrespective of the position of the wearer. For example, the high leg openings in the front of the diaper is more conducive to comfortable sitting by reducing the stress at the upper groin/thigh area than prior art diapers.

Further still, as will be seen and described later, the leg openings 40 are not elasticized around their entire perimeter, as has characterized many prior art diapers. This feature reduces the tendency for the leg openings to bind or chafe the wearer's legs, without any increased tendency for diaper leakage at the leg openings. To achieve that end, the intermediate section 26 of the diaper 22 is itself elasticized along its length immediately adjacent the marginal edge along each long side 26A and 26B and with only the end portions 26C and 26D of the intermediate section 26 adhesively secured to the front and rear sections 22 and 24, respectively. Moreover, as will be described later, the means for elasticizing those edges are pre-tensioned elastic threads or strands. When the tension on those elastic threads is released, they shrink to cause the marginal edges along the mid-section to "stand up." This action forms a pair of respective side barrier walls that closely conform to the wearer's crotch, and effectively forms a "bucket" for receipt and trapping of the waste product(s) by the absorbent core (to be described later) located within the intermediate section. This stand-up wall feature of the intermediate section is likely to eliminate the need for the inclusion of the somewhat complex and somewhat costly prior art "standing leg cuffs," although such standing leg cuffs can be added to the diaper, if desired, in the interests of further protection from leakage. In fact, the embodiment of FIGS. 20–22 include such optional standing leg cuffs.

Referring now to FIGS. 3 and 8–22, the details of various exemplary embodiments of diapers/adult briefs constructed in accordance with this invention will now be described. However, before doing that it should be noted that in accordance with the method aspects of this invention the front and rear sections of the diapers/adult briefs are formed as plural integral panel or sheet unit and each such unit is moved down one assembly line for merger with a series of intermediate sections moved down another assembly line. The specifics of the manufacturing methods will be described later. Suffice it for now to state that the integral panel units forming the front and rear sections of the articles 20 are carried along one assembly line to be deposited and adhesively secured spaced from each other at respective leading and trailing ends of an intermediate section of a string of such intermediate sections moving down another assembly line. Then the two integral panel units which are adhesively secured to the leading and trailing ends of the intermediate section are each severed transversely to complete one diaper. The severing action to form the front and rear sections from the integral panel units occurs across two integral units at one time to form each diaper. In particular, the downstream portion of the downstream panel unit forms the rear section of one diaper while the upstream portion of the downstream panel unit forms the front section of the next succeeding diaper and the downstream portion of the upstream panel unit forms the rear section of that next succeeding diaper.

Figure 3:
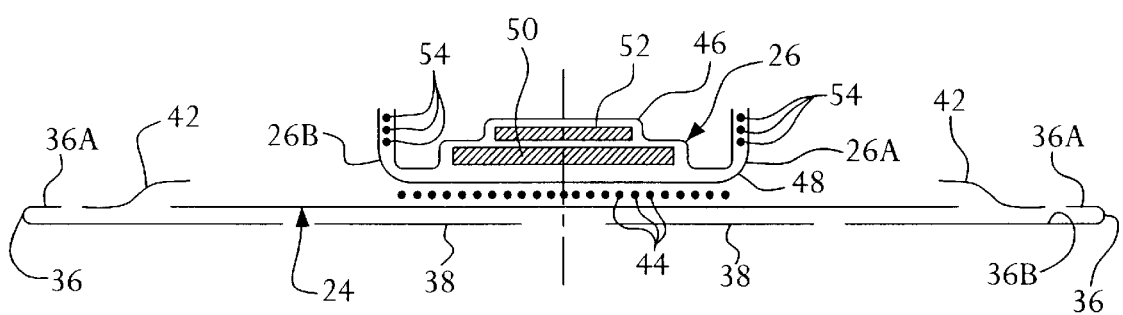
FIG. 3 is an enlarged sectional view, not to scale, taken through the rear section of the absorbent article along line 3—3 of FIG. 2, but before the front and rear sections are connected together, and with optional "landing zone" portions of the front section being included in this figure for illustrative purposes.

In FIG. 3 there is shown an enlarged sectional view, not to scale, taken through the rear section and contiguous portion of the intermediate section of the diaper taken along line 3—3 of FIG. 2, but before the front and rear sections are connected together by the fastening tapes 36, and with optional "landing zone" portions 38 forming a portion of the front section 22 being included in this figure for illustrative purposes only. As can be seen therein the rear section 24 in this illustrative embodiment is formed of a single layer or panel of a non-woven material, such as a conventional spunbond-meltblown-spunbond (SMS) material sold under the trade designation polypropylene non-woven by Avgol of Holon, Israel. The rear section SMS material may be of any suitable weight, e.g., 13.5 gsm. Alternatively the rear section panel may be a poly-film, sold under the trade designation polyethylene cast film XP-1842D by Huntsman Packaging of Williamsburg, Va. The rear section film material may be of any suitable thickness, e.g., 0.6 mil.

The front section 22 is constructed in the same manner as the rear section 24 in this embodiment. In fact, it is contemplated that every embodiment of a diaper/adult brief constructed in accordance with this invention have a front section and a rear section formed of the same materials, although such is not mandatory.

Attached to the side marginal edges 24C and 24D of the rear section 24 are the heretofore identified fastening tapes 36. In this embodiment each of the tapes is an adhesive tape, such as that sold under the trade designation KN1546 polypropylene film by 3M Corporation of St. Paul, Minn. The free end 36A (FIGS. 2–3) of each tape 36 is folded over itself so that the adhesive on its inner surface 36B bonds the folded over free end 36A to itself to form a finger lift tab to facilitate the securement and release of the fastening tape 36 to its associated landing zone 38 on the diaper's front section 22. Respective conventional release strips 42 are secured to the inner surface of the panel forming the rear section 24 at the location of the adhesive strips 36 to enable the adhesive strips to be initially releasably secured thereto as is conventional (e.g., to protect the adhesive on the strip from becoming contaminated or otherwise degraded).

The trailing end portion 34 of the intermediate section 26 is fixedly secured to the inner surface of the rear section 24 at the middle thereof and with the edge 26D of the intermediate section aligned with the top edge 24A of the rear section. This securement is accomplished by the use of a conventional construction adhesive 44, such as that sold under the trade designation #34-5634 hot melt by National Starch and Chemical Company of Bridgewater, N.J. The construction adhesive 44 can be sprayed on or deposited in straight or arcuate lines across the central portion of the intermediate sections, but not on the intermediate section portions that are contiguous with the intermediate section's marginal edges 26A and 26B. This feature enables the marginal edges of the intermediate section 26 to flex upward to form a pair of upstanding barrier walls 26A and 26B for the crotch region of the diaper, as will be described later.

In the embodiment shown in FIG. 3 the intermediate section 26 comprises a moisture-pervious cover-stock layer 46 and a moisture impervious barrier layer 48 which are each of rectangular shape and of the same size. The cover-stock layer can be of any suitable construction, such as a conventional non-woven material. One particularly suitable material is spunbonded polypropylene (SBBP) non-woven, such as sold under the trade designation 15 gsm polypropylene non-woven by Avgol of Holon, Israel. The barrier layer 48 can also be of any suitable construction, e.g., a conventional polyethylene film or a conventional polylaminate (PLAM). One particularly suitable film is that sold under the trade designation 1.0 mil cast polyethylene XC3-222-1491.1 by Huntsman Packaging of Williamsburg, Va. One particularly suitable PLAM is that sold under the trade designation XLAM #8B4535 by Huntsman Packaging of Williamsburg, Va. A conventional fluid absorbent core 50 (FIGS. 2, 3 and 4) of generally rectangular shape is interposed between the cover-stock layer 46 and the moisture barrier layer 48. The width of the core is less than that of the cover-stock layer and moisture barrier layer so that the longitudinally extending marginal sides 26C and 26D of the intermediate section are extremely flexible and conformable to the anatomy of the wearer, as will be described later. As can be seen in FIG. 3 the construction adhesive 44 engages the outer surface of the barrier layer 48 between those marginal edges 26A and 26B. The core is of any suitable construction such as a fluff, e.g., comminuted wood pulp or other cellulosic fibers. Enhanced absorbency for the core can be accomplished by use of an air-laid super absorbent material, or by the inclusion of absorbency enhancers, e.g., materials sometimes referred to as "super-absorbent-polymers" (which may be in the form of particles or fibers) with other absorbent materials, Examples of super absorbent materials are hydrogel polymer particulates, sometimes referred to as "SAP," and hydrogel polymer fibers, sometimes referred to as "SAF." The fluff for the core serves as a means for quickly absorbing the liquid transferred to it. Unfortunately, while fluff is suitable for the task of quick absorption it is somewhat deficient from the standpoint of liquid retention and ability to accommodate repeated insults. SAP on the other hand, has the ability to retain absorbed liquid and to handle repeated insults. The drawback with SAP and SAF are their slowness in absorbing liquid.

Accordingly, in the embodiment of the invention shown in FIG. 3 the intermediate section also includes an optional fluid acquisition or surge layer 52 (also sometimes called a "transfer" layer) disposed over the core 50. The acquisition layers can be of any suitable material such as a woven, non-woven or carded fibrous material. One particularly suitable material is TABICO FF, sold by Polymer Group, Inc. of Charleston, S.C. The acquisition layer 52 serves to quickly absorb the liquid through the cover stock 46 for temporary retention (e.g., to act as a temporary reservoir), and to transfer that liquid into the underlying core 50 at a rate at which the core can absorb for final or permanent retention. The fluid acquisition layer 52 is in the form of a rectangular strip of slightly less width than the core 50 and which extends for a substantial length of the core centered over it in the area which will receive the urine/feces insult.

Figure 5:
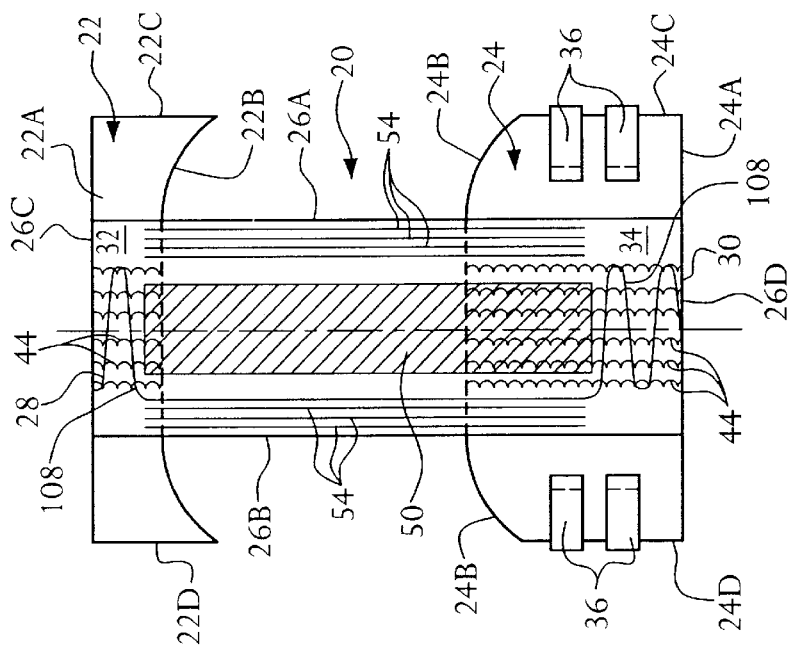
FIG. 5 is a top plan view of an later step in the manufacturing process shown in FIG. 4, but after severing of one of the completed articles from the manufacturing line.
Figure 4:
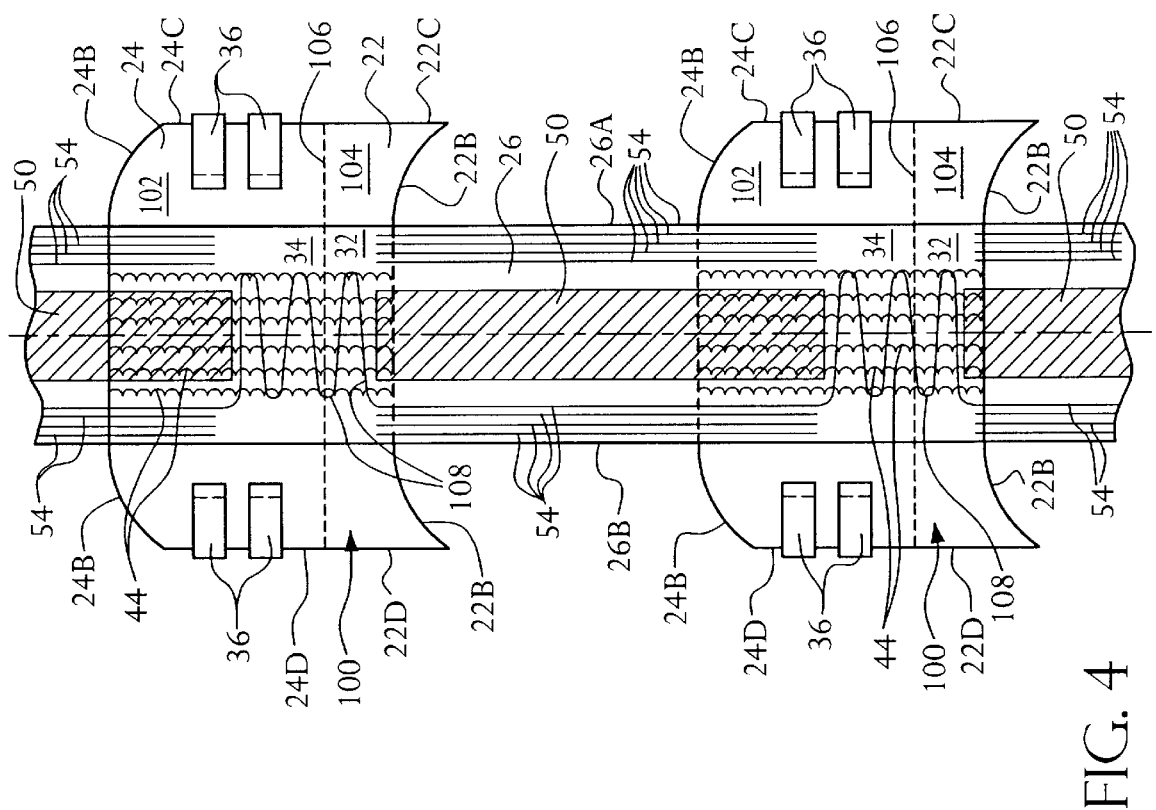
FIG. 4 is a top plan view of an initial step in a continuous manufacturing process for assembling the front and rear sections to the intermediate section to sequentially form embodiments of the absorbent article, e.g., diaper, shown in FIG. 1, and wherein the front and rear sections of each article are each of a "one-piece" panel construction.

As mentioned earlier the intermediate section is elasticized along its marginal edges 26A and 26B to enable the intermediate section when worn to form a cup-shaped or bucket shaped arrangement having a pair of upstanding barrier walls. To that end plural elongated pre-tensioned threads or strands 54 of any suitable elastic material are adhesively secured between the marginal edges of the coverstock layer 46 and the barrier layer 48. If desired, one or more of these prestress threads/strands can be extended into the area of the intermediate section 26 adjacent its leading end 26C to form the heretofore identified front elastic waist section 28, and can also be extended into the area of the intermediate section 26 adjacent its trailing end 26D to form the heretofore identified rear elastic waist section 30 (as shown in FIGS. 4 and 5). The strands 54 can be of any suitable elastic material. One such material is Lycra XA sold under the trade designation of Decitex 740 by E. I. DuPont DeNemours and Company, Inc. of Wilmington, Del.

Figure 8:
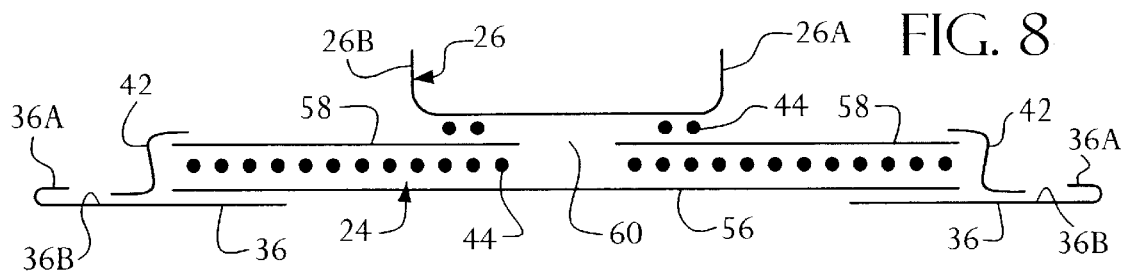
FIG. 8 is an enlarged sectional view similar to that of FIG. 3, with the exception of illustrating the absorbent system, but showing an alternative embodiment of the subject invention, with the intermediate section being shown schematically and with the article's front and rear sections each being formed of a poly in-line laminate and arranged to be secured together by adhesive fastening tapes.

In FIG. 8 there is shown another alternative embodiment of the diaper/adult brief constructed in accordance with this invention. The view in FIG. 8 is similar to that of FIG. 3, except that the intermediate section 26 is merely shown schematically by a U-shaped line. Thus, it should be understood that the intermediate section can be constructed identically to the embodiment of FIG. 3 or in accordance with any other embodiment thereof contemplated by this invention. Moreover, the common components of the embodiments of FIGS. 3 and 8 will be given the same reference numbers and the details of their construction and operation will not be reiterated in the interests of brevity. Thus, as can be seen the rear section panel 24 is in this embodiment made up of a multi-layered panel. That panel comprises an outer layer 56 in the form of a plastic film, e.g., a polyethylene film, such as that sold under the trade designation 1.0 mil cast polyethylene XC3-222-1491.1 by Huntsman Packaging of Williamsburg, Va. The inner layer 58 of the panel is in the form of a non-woven, e.g., a spunbond-meltblown-spunbond 13.5 gsm material that is sold under the trade designation polypropylene non-woven by Avgol of Holon, Israel. The two layers are adhesively secured together by any suitable construction adhesive 44.

The fabrication of the panels forming the diaper/adult brief of this embodiment can be accomplished in various ways, one of which will be described later. Suffice it for now to state that the non-woven layer 58 is split into two portions leaving a gap 60 therebetween before it is adhesively bonded to the film layer 56 in order to save material, and without any sacrifice in functionality. In this regard as can be seen in FIG. 8 the portion of the panels making up the front and rear sections having the gaps 60 will be covered by the intermediate section 26 when that section is secured thereto by the construction adhesive 44.

As should be appreciated by those skilled in the art since the outer surface of the panels making up the diaper's front and rear sections of the embodiment of FIG. 8 are each film 56, it may not be necessary to include any landing zones 38 on the front section to releasably accept adhesive type fastening tapes 36. Thus, in this embodiment no such landing zones are shown.

Figure 9:
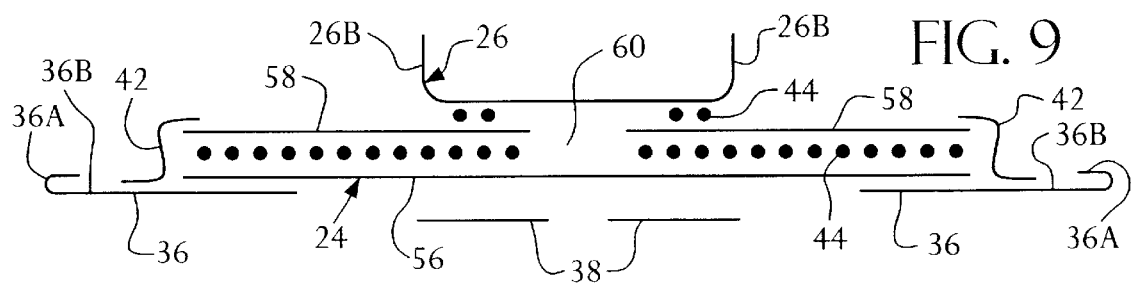
FIG. 9 is an enlarged sectional view similar to that of FIGS. 3 and 8, with the exception of illustrating the absorbent system, but showing another alternative embodiment of the subject invention, with the intermediate section being shown schematically and with the article's front and rear sections each being formed of a poly in-line laminate and arranged to be secured together by adhesive fastening tapes engaging respective "landing zones" on the front section (the landing zones being included in this figure for illustrative purposes)

In FIG. 9, however, there is shown an embodiment of a diaper/adult brief having such landing zones. The embodiment shown in FIG. 9 is identical to that shown in FIG. 8, except for the inclusion of a pair of landing zones 38 (shown illustratively in this figure) adhesively secured on the film layer 56 of the front section 22. The inclusion of those landing zones enables the use of a thinner gauge polyethylene film material for the outer layer 56, e.g., a 0.8 mil material instead of the 1.0 mil material described with reference to FIG. 8. The landing zones may be of a suitable material, such as BOPP (Bi-axially orientated Polypropylene film) sold under the trade designation KR0882 by 3M Corporation of St. Paul, Minn. and are adhesively secured on the outer surface 56 of the front section 22.

Figure 10:
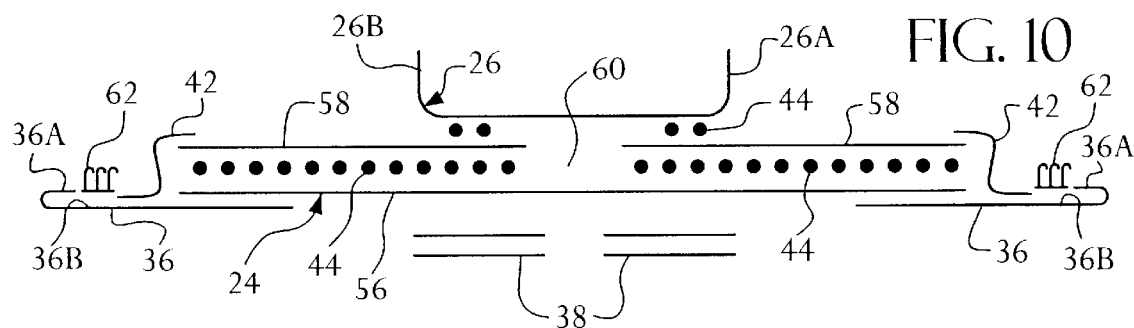
FIG. 10 is an enlarged sectional view similar to that of FIGS. 3, 8 and 9, with the exception of illustrating the absorbent system, but showing still another alternative embodiment of the subject invention, with the intermediate section being shown schematically and with the article's front and rear sections each being formed of a poly in-line laminate and arranged to be secured together by hook-like fastening tapes engaging respective loop-like or plush "landing zones" on the front section (the landing zones being included in this figure for illustrative purposes)

In FIG. 10, there is shown another embodiment of a diaper/adult brief like that of FIG. 9, but utilizing plural multi-hook type of mounting tapes 36, instead of the adhesive tapes described heretofore, and a different type of cooperating landing zones. Other than those differences the panels forming the diaper of FIG. 10 are identical to that of FIG. 9. The multi-hook tapes 36 of this embodiment basically comprise the heretofore described adhesive tapes, except for the inclusion of a multi-hook patch 62 adhesively secured to the adhesive layer 36B of each tape 36 between the folded over free end 36A and the release tape 42. The multi-hook patches can be of any suitable construction, such as that sold under the trade designation CS-1010 by 3M Corporation of St. Paul, Minn. Since the mounting tapes 36 make use of the multi-hook patches 62, the front section of the diaper of this embodiment includes a pair of landing zones 38 that are particularly constructed to accommodate those multi-hooks. To that end the landing zones 40 may be constructed of a plush or multi-loop material, e.g, a poly and non-woven or knit material adhesively secured onto the layer 56 of the front section. One particularly suitable material for the landing zones is that sold under the trade designation EBL by 3M Corporation of St. Paul, Minn.

Figure 11:
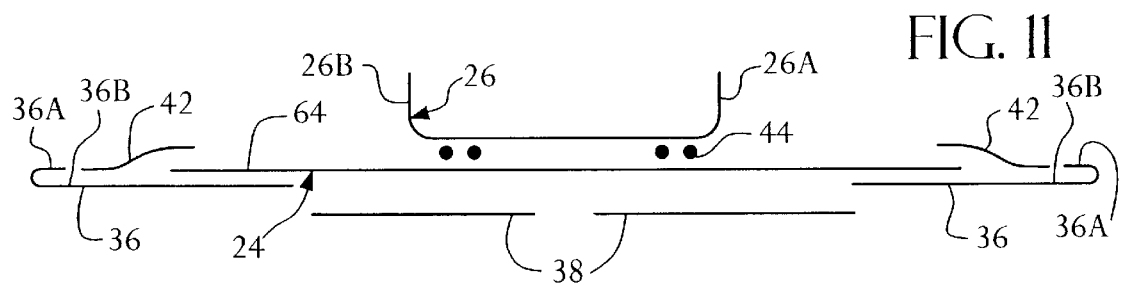
FIG. 11 is an enlarged sectional view similar to that of FIGS. 3 and 8–10, with the exception of illustrating the absorbent system, but showing still another alternative embodiment of the subject invention with the intermediate section being shown schematically and with the article's front and rear sections each being formed of a cloth-like non-woven material and arranged to be secured together by adhesive fastening tapes engaging respective "landing zones" on the front section (the landing zones being included in this figure for illustrative purposes)

In FIG. 11 there is shown an embodiment of the diaper/adult brief constructed in accordance with this invention similar to that of FIG. 3, except that the intermediate section 26 is merely shown schematically by a U-shaped line. In this embodiment the rear section panel 24 is made up of a single layer of a cloth-like non-woven material 64, e.g., SMS. One particularly suitable material is a 22 gsm SMS, such as that sold under the trade designation polypropylene non-woven by Avgol of Holon, Israel.

Figure 12:
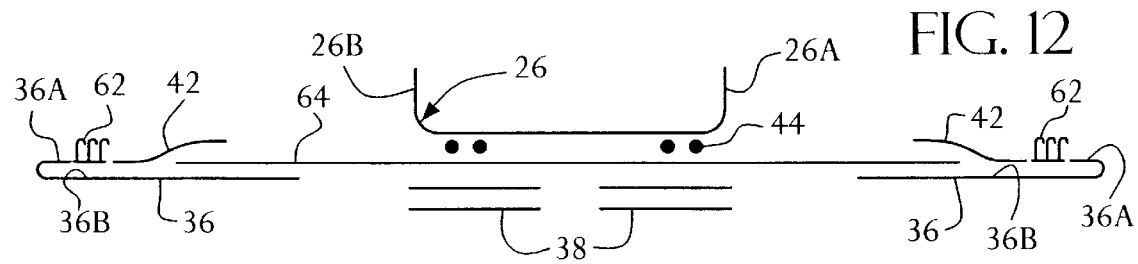
FIG. 12 is an enlarged sectional view similar to that of FIGS. 3 and 8–11, with the exception of illustrating the absorbent system, but showing still another alternative embodiment of the subject invention with the intermediate section being shown schematically and with the article's front and rear sections each being formed of a cloth-like non-woven material and arranged to be secured together by hook-like fastening tapes engaging respective loop-like or plush "landing zones" on the front section (the landing zones being included in this figure for illustrative purposes)

In FIG. 12 there is shown another alternative embodiment of a diaper/adult brief constructed in accordance with this invention. The embodiment shown in FIG. 12 is identical to that shown in FIG. 11, except for the inclusion of multi-hook patches 62 adhesively secured to fastening tapes 36 and multi-loop or plush-like landing zones 38 like that of FIG. 10.

Figure 13:
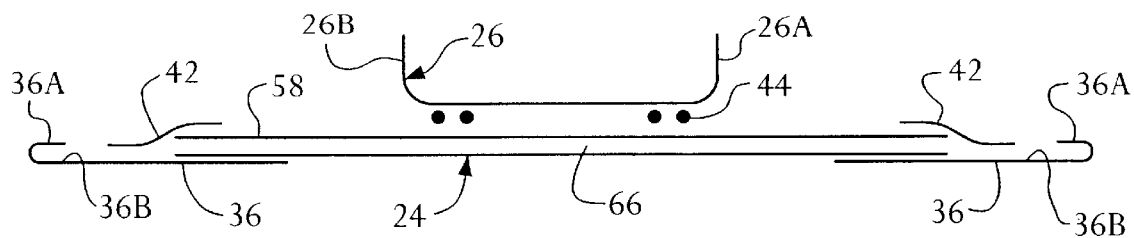
FIG. 13 is an enlarged sectional view similar to that of FIGS. 3 and 8–12, with the exception of illustrating the absorbent system, but showing an alternative embodiment of the subject invention, with the intermediate section being shown schematically and with the article's front and rear sections each being formed of a poly-laminate (PLAM) and arranged to be secured together by adhesive fastening tapes.

In FIG. 13 there is shown another alternative embodiment of a diaper/adult brief constructed in accordance with this invention. The embodiment shown in FIG. 13 is identical to that shown in FIG. 8, except that the multi-layer panel material is a prefabricated or preassembled poly-laminate (PLAM) 66. The PLAM has an film outer layer 56 and a non-woven inner layer 58. One particularly suitable PLAM material is that sold under the trade designation XLAM #8B4535 by Huntsman Packaging of Williamsburg, Va.

Figure 14:
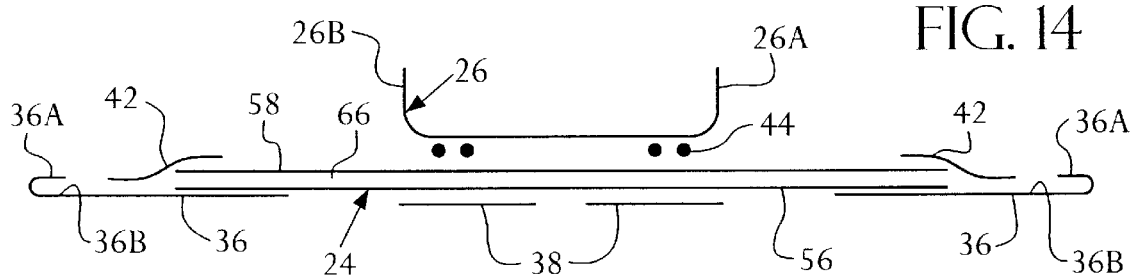
FIG. 14 is an enlarged sectional view similar to that of FIGS. 3 and 8–13, with the exception of illustrating the absorbent system, but showing another alternative embodiment of the subject invention, with the intermediate section being shown schematically and with the article's front and rear sections each being formed of a poly-laminate (PLAM) and arranged to be secured together by adhesive fastening tapes engaging respective "landing zones" on the front section (the landing zones being included in this figure for illustrative purposes)

In FIG. 14 there is shown another alternative embodiment of a diaper/adult brief constructed in accordance with this invention. The embodiment shown in FIG. 14 is identical to that shown in FIG. 13, except for the inclusion of adhesive fastening tapes 36 and landing zones 38 like that of FIG. 9.

Figure 15:
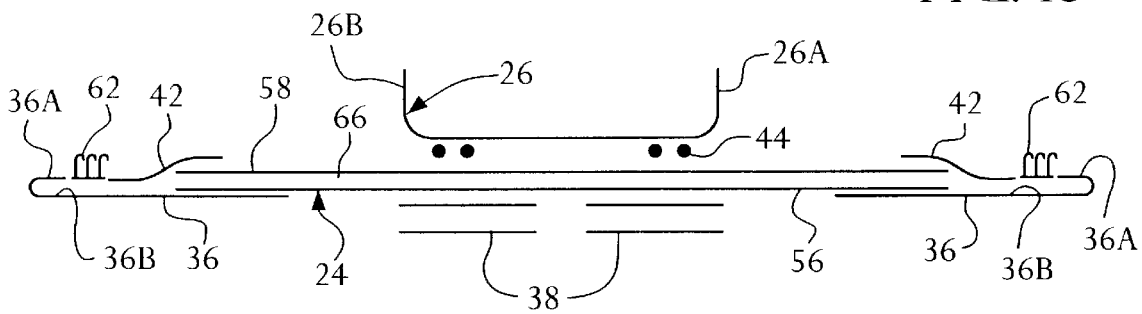
FIG. 15 is an enlarged sectional view similar to that of FIGS. 3 and 8–14, with the exception of illustrating the absorbent system, but showing still another alternative embodiment of the subject invention, with the intermediate section being shown schematically and with the article's front and rear sections each being formed of a poly-laminate (PLAM) and arranged to be secured together by hook-like fastening tapes engaging respective loop-like or plush "landing zones" on the front section (the landing zones being included in this figure for illustrative purposes)

In FIG. 15 there is shown another alternative embodiment of a diaper/adult brief constructed in accordance with this invention. The embodiment shown in FIG. 15 is identical to that shown in FIG. 13, except for the inclusion of multi-hook patches 62 adhesively secured to fastening tapes 36 and landing zones 38 like that of FIG. 10.

Figure 16:
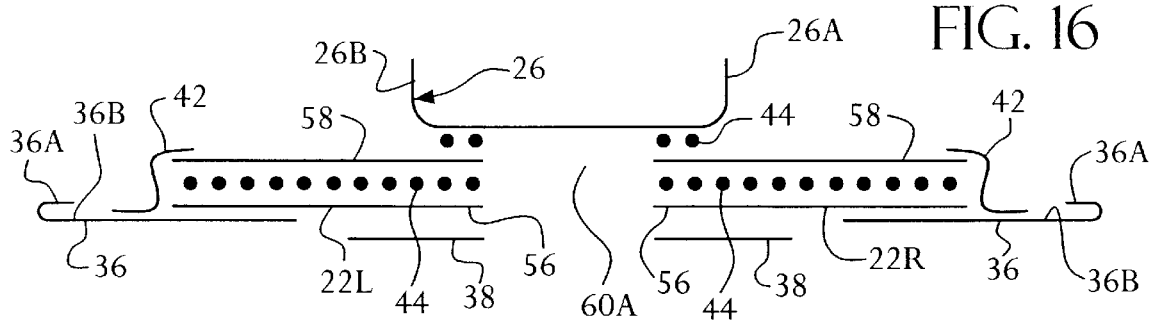
FIG. 16 is an enlarged sectional view similar to that of FIG. 9, with the exception of illustrating the absorbent system, but showing an alternative embodiment of the subject invention like that of FIG. 9, but with the intermediate section being shown schematically and with the article's front and rear sections each being formed of a pair of split, mirror image panels of poly in-line laminate secured along their inner marginal edges to the intermediate section, and with the front and rear sections so connected being arranged to be secured together by adhesive fastening tapes.

In FIG. 16, there is shown an embodiment of a diaper/adult brief identical to that of FIG. 9, except for the fact that the front section 22 is formed of a pair of split or mirror image panels and the rear section 24 is also formed of a pair of split or mirror image panels. The construction of each of the split panels is the same as the construction described with reference to FIG. 9, i.e., includes an outer film layer 56 and an inner non-woven layer 58 adhesively secured together by a construction adhesive 44. The manner of forming this embodiment of the diaper/adult brief will be described later. Suffice it for now to state that the front section 22 is formed of two split panels 22R and 22L (FIGS. 6 and 7) that are separated by a gap 60A. The rear panel 24 is also formed of two split panels 24R and 24L that are separated by a gap 60A. The leading end portion 32 of the intermediate section 26 is located between and adhesively secured by the construction adhesive 44 to the inner marginal edges of the two split panels 22R and 22L. Thus, the leading end of the intermediate section 26 fills the gap 60A between those split panels to complete the front section 22 of the diaper/adult brief 20. In a similar manner the trailing end 34 of the intermediate section 26 is located between and adhesively secured by the construction adhesive 44 to the inner marginal edges of the two split panels 24R and 24L. Thus, the trailing end of the intermediate section 26 fills the gap 60A between those split panels to complete the rear section 24 of the diaper/adult brief 20. This arrangement saves the front and rear section material which would have otherwise been in the gap 60A since the gap is covered by the intermediate section 26.

It should be pointed out at this juncture that while only the embodiment FIG. 16 is illustrated in the figures as being manufactured by use of a split, mirror image pair of panels to form the front and rear sections of the article 20, this invention contemplates that any of the embodiments of the articles shown and described herein can make use of split panels instead of the integral panels illustrated and described heretofore.

In FIGS. 17–22 there are shown various alternative constructions for the intermediate section 26 that can be used in any embodiment of a diaper/adult brief constructed in accordance with this invention. In particular, in FIG. 17 there is shown an intermediate section 26 having a barrier layer 48 of 0.8 mil polyethylene film such as that sold under the trade designation cast polyethylene by Huntsman Packaging of Williamsburg, Va., and a cover-stock layer 46 of 15 gsm spunbond polypropylene such as that sold under the trade designation polypropylene non-woven by Avgol of Holon, Israel. A fluid acquisition layer 52 of is located under the spunbond cover-stock and above an absorbent core 50.

Figure 17:
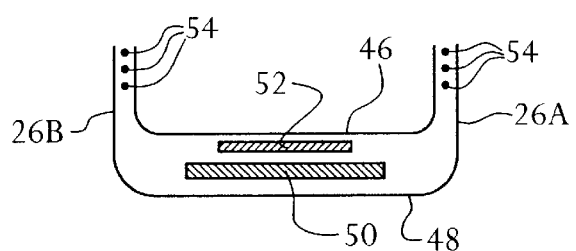
FIG. 17 is an enlarged sectional view of the embodiment of the intermediate section shown in FIG. 3, excluding the panels and attachment system.
Figure 18:
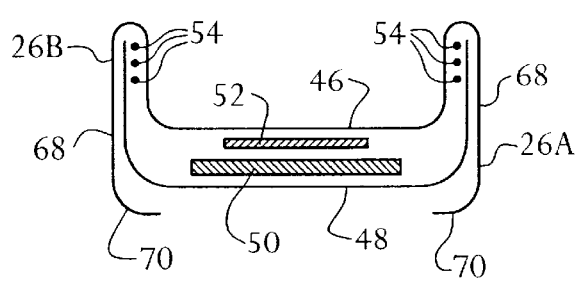
FIG. 18 is an enlarged sectional view, like that of FIG. 17, but showing an alternative intermediate section, excluding the panels and attachment system, constructed in accordance with this invention and useful in any of the embodiments of the absorbent article shown in FIGS. 8–15.

In FIG. 18 there is shown an alternative embodiment of the intermediate section shown in FIG. 17. In this embodiment the cover-stock layer 46 is folded over itself at each side to form a pair of flanges 68, each covering a respective one of the marginal edges of the polyethylene film barrier layer 48 to form a cloth-like surface for the intermediate section barrier walls 26A and 26B. This feature provides a comfortable interface for engagement with the skin of the wearer at the legs. The free end portion 70 of the cover-stock layer 46 is folded under the central portion of the barrier layer 48 and is left untreated for securement by the construction adhesive 44 to the panel(s) forming the front and rear sections of the article 20. In this embodiment, the barrier layer 48 can be of lesser thickness, e.g., 0.6 mil, polyethylene film than in the embodiment of FIG. 17. The cover-stock layer 46 in the middle of the insert (i.e., between the walls 26A and 26B and above the acquisition layer and the core) is zone coated, as is a conventional practice for such cover-stock materials for use in diapers, etc.

Figure 19:
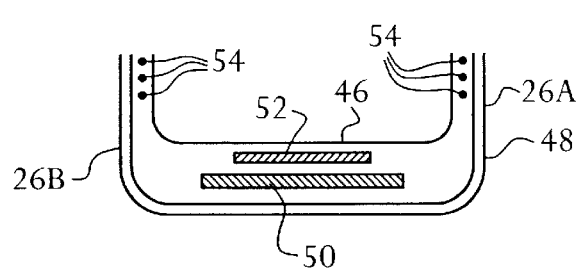
FIG. 19 is an enlarged sectional view, like that of FIGS. 17 and 18, but showing another alternative intermediate section, excluding the panels and attachment system, constructed in accordance with this invention and useful in any of the embodiments of the absorbent article shown in FIGS. 8–15.

In FIG. 19 there is shown yet another alternative embodiment of an intermediate section 26. The intermediate section of FIG. 19 is similar to that shown in FIG. 17 except that the barrier layer instead of being a 0.8 mil polyethylene film is a poly-laminate (PLAM) such as that sold under the trade designation XLAM #8B4535 by Huntsman Packaging of Williamsburg, Va.

Figure 20:
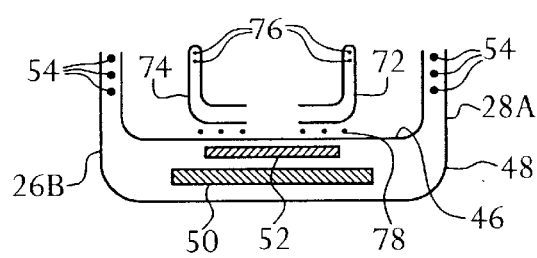
FIG. 20 is an enlarged sectional view, like that of FIGS. 17–19, but showing an another alternative intermediate section, excluding the panels and attachment system, constructed in accordance with this invention and useful in any of the embodiments of the absorbent article shown in FIGS. 8–15.
Figure 21:
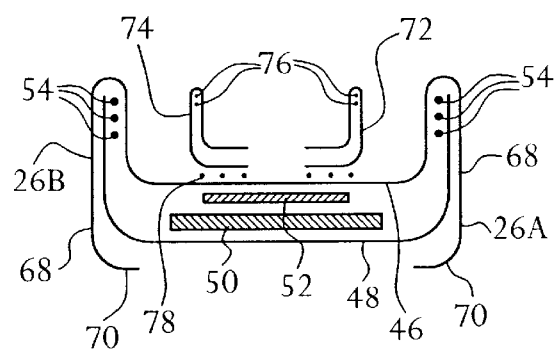
FIG. 21 is an enlarged sectional view, like that of FIGS. 17–20, but showing another alternative intermediate section, excluding the panels and attachment system, constructed in accordance with this invention and useful in any of the embodiments of the absorbent article shown in FIGS. 8–15.
Figure 22:
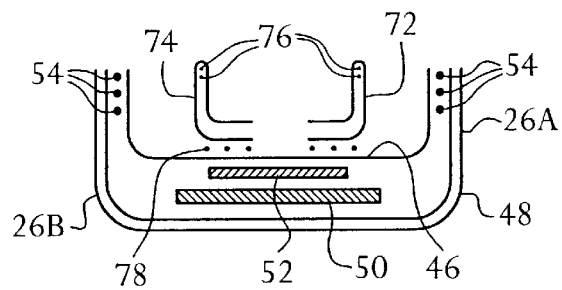
FIG. 22 is an enlarged sectional view, like that of FIGS. 17–21, but showing another alternative intermediate section, excluding the panels and attachment system, constructed in accordance with this invention and useful in any of the embodiments of the absorbent article shown in FIGS. 8–15.

In FIGS. 20–22 there are shown yet other alternative embodiments of intermediate sections constructed in accordance with this invention. The embodiments of FIGS. 20–22 are identical to those of FIGS. 17–19 except for the inclusion of a pair of conventional standing leg cuffs 72 and 74. As can be seen, each of the standing leg cuffs 72 and 74 is folded over itself to form a generally L-shaped member and which includes at least two elongated pre-tensioned elastic strands 76 extending down the length thereof at the portion which is folded over. The elastic strands 76 may be of any suitable type such as Lycra sold under the trade designation of Decitex 680 by E. I. Dupont DeNemours and Company, Inc. of Wilmington, Del. Each of the standing leg cuffs is fixedly secured to the central portion of the cover-stock 46 by a conventional construction adhesive 78. The standing leg cuffs 72 and 74 may be formed of any suitable material, e.g., a spunbond-meltblown-spunbond (or other non-woven material) such as that sold under the trade designation polypropylene non-woven by Avgol of Holon, Israel.

The diapers/adult briefs can be made in various ways in accordance with the method(s) of this invention, depending upon whether or not the front and rear sections 22 and 24, respectively, of the article are to be formed of a single panel or a pair or split, mirror image panels. In the embodiments of the articles shown in FIGS. 3–5 and 8–15 the articles are manufactured from single panel units to form the front and rear sections, whereas the article shown in FIGS. 6, 7 and 16 is manufactured from a pair of split, mirror image panels.

The manufacturing process for making a unitary panel or "one-piece" diaper like that shown in FIG. 8 will now be described with reference to FIGS. 4 and 5. That method comprises the steps of unwinding a spunbond-meltblown-spunbond or other non-woven web of material from a reel (not shown), slitting the web in half to form two web sections 58 (FIG. 8) separated by a gap 60. The construction adhesive 44 is applied to the underside of both of the split web sections 58. The poly-film 56 layer is unrolled from a reel (not shown) and is laminated to the two split non-woven web sections by means of the construction adhesive 44. The resulting laminated web with the spaced apart non-woven layer 58 is then brought to a station where there is registered and applied a pair of fastening tapes 36 and associated release strips 42 to each marginal side edge of the now unitary laminated web. The end portion of each of the fastening tapes is folded over itself, as described earlier. The assembled laminated web with the fastening and release tapes located thereon at spaced locations is then die cut to form an integral panel or sheet unit 100 (FIG. 4). Each die cut sheet unit 100 serves to form the front section 22 of one diaper and the rear section 24 of the next succeeding diaper. To that end, and in accordance with a preferred aspect of the invention, the die cut sheet or panel unit 100 includes a pair of areas 102 and 104 which merge with each other along a transverse interface line 106. The area 102 is located between the interface line 106, the two marginal linear side edges 24C and 24D and the arcuate convex edge 24B and defines the heretofore identified rear section 24 of the diaper 20. The area bounded by the interface line 106, the two side edges of 22C and 22D and the concave arcuate edge 22B define the heretofore front section 22 of the diaper 20.

All of the foregoing steps to form the panel units 100 can be undertaken along one continuous assembly line. Moreover, each of the panel units 100 is of a complementary shape, i.e., the edges 22B and 24B are complementary, so that the panels 100 can be sequentially die cut from the laminated web of the non-woven material and the film, without any wastage. Then each die cut panel unit can be carried to the assembly line conveying the series of intermediate sections 26 (as will be described later).

The intermediate sections are fabricated and assembled from their various components to form a sequential interconnected series of intermediate sections, with the trailing end 34 of one intermediate section 26 forming the leading end 32 of the next succeeding section when the sections are severed from one another. The intermediate section 26 can be fabricated in various ways, depending upon their construction. For example, a diaper having an intermediate section 26 like that shown in FIGS. 3 and 8 is fabricated and assembled as follows. A web of material forming moisture barrier layer 48 is provided (e.g., from a reel) and a series of absorbent cores 50 are deposited thereon. A series of acquisition layers 52 are deposited over the cores, and a web of material forming the cover-stock layer 46 is deposited thereover.

In accordance with one preferred aspect of this invention plural elastic, e.g., Lycra, threads 54 are extended and adhesively secured between the marginal edges of the cover-stock layer 46 and the moisture barrier layer 48. These elastic threads may be discontinuous or continuous (i.e., they extend from one intermediate section to the next and so on). Moreover, they are pre-tensioned so that when tension is released (when the diaper is severed and completed—as will be described later) they tend to contract, which action causes the peripheral edges of the intermediate section of the diaper to bend upward to form the pair of walls 26A and 26B like shown and described earlier. However, when the inserts 26 are sequentially located in the assembly line before the diapers are severed from one another tension remains applied to the elastic strands so that each intermediate section is of a generally planar configuration.

If the diaper 20 is to include an elasticized waist area, i.e., elastic sections 28 and 30, like that described heretofore with respect to FIG. 1, one or more of the continuous elastic strands 54 that are extended along the outer marginal edges of the intermediate sections are brought inward in a zig-zag configuration or pattern in 108 (FIG. 4) the area of the intermediate section 26 centered over the line defining the trailing edge of one intermediate section and the leading edge of the next succeeding section. When the diaper 20 is severed from the remaining diapers the zig-zag area of the pre-tensioned thread 54 will shrink and cause the top edge of the front section 22 and the top edge of the rear section 24 to gather at 28 and 30 respectively.

The series of assembled intermediate sections 26 are conveyed to a position wherein each section is adapted to receive a pair of die cut panel units 100 provided from the other assembly line. To that end, the speed of the two assembly lines is coordinated so that the leading (downstream-most) die-cut panel unit 100 is centered over the leading portion 32 of the first (downstream-most) of the intermediate sections 26 of the line of intermediate sections and with the interface line 106 being axially aligned with the leading edge of that first intermediate section. Immediately prior to that alignment, a construction adhesive 44 (e.g., a series of arcuate lines of adhesive—see FIG. 4) is applied to the leading end portion of the first of the intermediate sections, whereupon when the panel unit 100 is brought into engagement therewith, it is adhesively secured thereto. The next successive die cut panel unit 100 is carried by its associated assembly line and speeded up so that it reaches the trailing end of the first intermediate section to which the upstream-most panel unit 100 had been secured. Prior to that occurring, the portion of the first intermediate section at the trailing edge thereof and the portion of the leading edge of the next successive intermediate section have the construction adhesive 44 applied thereto in the same manner. Accordingly, when the next successive die cut panel unit 100 reaches the trailing end portion 34 of the first intermediate section so that its interface line 106 is aligned with the trailing edge of the first intermediate section and the leading edge of the second intermediate section it can be fixedly secured thereto like shown in FIG. 4.

Then the merger line 106 in the first die-cut panel unit 100 and the merger line 106 in the next succeeding panel unit are severed thereacross (e.g., die-cut). This action separates the portions 102 and 104 of each panel unit to complete the formation of a diaper 20 as shown in FIG. 5. The next succeeding diaper 20 is formed in an identical manner and this process continues until no further diapers are desired to be produced.

In FIGS. 6 and 7 there is shown the manufacturing process for forming a diaper/adult brief whose front and rear panels are each formed of a pair of split, mirror image panels, like that shown and described with reference to the embodiment of FIG. 16. In the interests of brevity the common features of the method depicted in FIGS. 6 and 7 and the method depicted in FIGS. 4 and 5, as just described, will not be reiterated and the same reference numbers will be given to the common features. The process is essentially the same as the method of FIGS. 4 and 5, except that the panel units 100 are replaced by split, mirror image units 200R and 200L. In particular, the unit 200R is composed of two areas 22R and 24R which merge with each other along a transverse interface line 106. The area 24R is located between the interface line 106, the marginal linear side edge 24C, the arcuate convex edge 24B and the linear inside edge portion 96R and defines the right side portion of the heretofore identified rear section of the diaper 20. The area 22R bounded by the interface line 106, the side edge of 22C, the concave arcuate edge 22B and the linear inside edge portion 97R and define the right side portion of the heretofore front section 22. The panel unit 200L is the mirror image of the panel unit 200R and is separated from it by the gap 60A. Thus, the panel unit 200L is composed of two areas 22L and 24L which merge with each other along a transverse interface line 106. The area 24L is located between the interface line 106, the marginal linear side edge 24D, the arcuate convex edge 24B and the linear inside edge portion 96L and defines the left side portion of the heretofore identified rear section 24 of the diaper 20. The area 22L bounded by the interface line 106, the side edge of 22D, the concave arcuate edge 22B and the linear inside edge portion 97L and define the left side portion of the front section 22. The two mirror image panel units 200R and 200L, once assembled, are carried down an assembly line side-by-side separated by the gap 60A for location and adhesive securement onto the leading end portion of one intermediate section, with the interface line 106 being coincident with the trailing edge of one intermediate section and the leading edge of the next successive intermediate section in the same manner as described with respect to the panel units 100. The next two assembled mirror image panel units 200R and 200L are carried down that assembly line side-by-side separated by the gap 60A for location and adhesive securement onto the trailing end portion of the one intermediate section, in the same manner as described with respect to the panel units 100. In the method shown in FIGS. 6 and 7 the construction adhesive 44 securing the split panel units to the intermediate section is deposited in a series of linear lines instead of the arcuate lines shown in FIGS. 4 and 5, but such an arrangement is merely exemplary of any pattern that the construction adhesive may be dispensed to secure the diaper's sections to one another.

Once the two pairs of mirror image panel units are secured to the respective leading and trailing ends of an intermediate section, they are severed along their interface lines 106 in the same manner as described with reference to FIGS. 4 and 5 to complete the diaper/adult brief.

As should be appreciated by those skilled in the art from the foregoing the absorbent articles of this invention are simple in construction, effective and are comfortable to wear. Moreover, they can be manufactured economically due to their simplified construction. For example, as discussed earlier the leg openings are not be elasticized around their entire perimeter as has characterized the prior art. This feature eliminates the somewhat complex prior art manufacturing step of disposing tensioned elastic threads around an arcuate path as the absorbent articles are moved along an assembly line. In contradistinction, since the subject invention makes use of linear elastic lines 54 which are only located on the intermediate section 26, they can be readily applied as the intermediate section is moved down the assembly line.

Further still and quite significantly, as will be appreciated from the description to follow since the absorbent articles of this invention are formed of respective individual sections which are secured together during the manufacturing/assembly process, the panels making up the various sections can be readily die cut and brought into engagement on an efficient and economical basis. In particular, in accordance with a preferred embodiment of this invention, the front and rear sections 22 and 24 are complementary shapes, so that a sheet of material making up the front section of a leading diaper in the assembly line and the rear section of the next succeeding diaper can be die-cut as a unit. This feature not only speeds up the manufacturing process but virtually eliminates any wastage of material and the concomitant steps of removing and disposing of the waste scraps (e.g., vacuum collection of leg cut-out material scraps and disposal/handling of such scraps).

Not only does the process of this invention result in little or no wastage of material, it is also very efficient to accomplish. In this regard, once the unit making up the front section's panel(s) of the leading diaper in the assembly line and the rear or back section's panel(s) of the next succeeding diaper has been die cut it is conveyed into engagement with the leading end portion of the first intermediate section of a moving line of sequentially located intermediate sections to adhesively secure it in place to the leading end portion of that first intermediate section. The sheet of material making up the front panel(s) of a next succeeding diaper in the assembly line and the rear panel(s) of the next (second) succeeding diaper is die-cut as a unit and conveyed into engagement with the trailing end portion of the first intermediate section of the moving line of sequentially located intermediate sections to adhesively secure that unit in place thereto. Then the interface or line separating the front and rear sections (panel(s)) of the sheet unit attached to the leading end of the first intermediate section is severed to separate those sections from each other. At the same time the interface or line separating the front and rear sections (panel(s)) of the unit secured to trailing end of the first intermediate section is severed to separate those sections from each other. This simultaneous dual severing action results in the creation of a completed diaper. The foregoing process can be repeated on a continuous basis for as long as desired to fabricate multiple succeeding diapers.

An additional advantage of the manufacturing process of this invention is its extreme flexibility to effect the efficient manufacture different types of diapers without substantial modification to the manufacturing equipment. In particular, the construction of the front and rear sections can be altered as desired to create different diapers or other similar absorbent articles. Different materials can be used to make the front and rear sections of the diaper. Different types of fastening tapes (e.g., adhesive, multi-hook, etc.,) can be used, "landing zones" can be incorporated into the front section to facilitate the releasable securement of the fastening tapes thereto and to enable repeated fastening and re-fastening, if desired. Elastic materials can be provided in either or both of the front and rear sections along their top edges in the interests of forming a more secure or closer fit. The shape of the front and rear sections can be readily altered, if desired, by the mere substitution of another die cutter to form the desired shape for the sheet unit making up the front section of a leading diaper and the rear section of the trailing diaper (although as discussed earlier it is preferable that the lower edge portion of the front panel be somewhat concave to result in a high leg opening in the interests of comfort). So too, the construction of the intermediate sections can be altered as desired, e.g., different materials can be used for the cover-stock and barrier walls, the core can be of different materials and shapes (e.g., hour-glass shaped instead of rectangular), a fluid acquisition layer of any particular material or construction may be incorporated into the intermediate section between the cover-stock and the core, etc., standing leg cuffs can be added, etc.

The altered sections, be they the front, rear or intermediate sections or any combination thereof, can be brought down their respective assembly lines for assembly (e.g., adhesive securement) to the each other and subsequent severing to complete the modified diapers.

Further economies can be achieved in the manufacturing process by making use of a pair of panels for the front section and a pair of panels for the rear section. This arrangement will save the material which would otherwise be located in the gap between the panels of the front section and the material which would otherwise be located in the gap between the panels of the rear section, but which gaps are filled by the presence of the intermediate section adhesively secured therein. Further still, the material making up the barrier wall in the crotch area, if a film, can be of lower gauge in the interest of economics, without the loss of functionality.

Without further elaboration the foregoing will so fully illustrate our invention that others may, by applying current or future knowledge, adopt the same for use under various conditions of service.

I claim:

1. A disposable absorbent article arranged to be worn by a wearer to trap and collect waste, said article comprising front section, a rear section and an intermediate section, said front section being formed of a single, flexible generally planar panel having a top edge, a bottom edge, a first side edge and an opposed second side edge, said bottom edge of said front section being of a generally arcuate concave shape having a first concave shaped end portion and a second concave shaped end portion, said first concave shaped end portion merging with said first side edge of said front section, said second concave shaped end portion merging with said second edge of said front section, said rear section being formed of a single, flexible generally planar panel having a top edge, a bottom edge, a first side edge and an opposed second side edge, said bottom edge of said rear section being of a generally arcuate convex shape having a first convex shaped end portion and a second convex shaped end portion, said first convex shaped end portion merging with said first side edge of said rear section, said second convex shaped end portion merging with said second side edge of said rear section, said bottom edge of said front section and said bottom edge of said rear section being complementary in shape to each other, said intermediate section being an elongated member formed of a flexible material having a first side edge, a second side edge and an pair of end edges, one portion of said intermediate section adjacent one of said pair of end edges being fixedly secured to said front section intermediate said first and second side edges of said front section, a second portion of said intermediate section adjacent the other of said pair of end edges being fixedly secured to said rear section intermediate said first and second side edges of said rear section, said first side edge of said front section being arranged to be releasably secured to said first side edge of said rear section, said second side edge of said front section being arranged to be releasably secured to said second side edge of said rear section to mount said disposable absorbent article on the wearer and to form first and second leg openings, said first leg opening defining a high cut at said front section and comprising said first concave shaped end portion of said bottom edge of said front section, an adjacent portion of said first side edge of said intermediate section, and said first convex shaped end portion of said bottom edge of said rear section, said second leg opening defining a high cut at said front section comprising said second concave shaped end portion of said bottom edge of said front section, an adjacent portion of said second side edge of said intermediate section, and said second convex shaped end portion of said bottom edge of said rear section, said intermediate section being elasticized adjacent said first and second side edges thereof to conform to the crotch of the wearer, said intermediate section being arranged to absorb and trap waste material therein.

2. The disposable absorbent article of claim 1 wherein said front section, said rear section and said intermediate section are fixedly secured together by an adhesive.

3. The disposable absorbent article of claim 1 wherein said front and rear sections are each constructed of a poly-laminate material comprising a layer of spunbond-meltblown-spunbond non-woven material and a layer of polyethylene film secured together.

4. The disposable absorbent article of claim 1 additionally comprising elongated elastic members extending along said first and second sides of said intermediate section, said elastic members being normally under tension to cause said intermediate section to assume a cup-like configuration having a pair of upstanding walls having an outer surface, said upstanding walls generally conforming to the crotch of the wearer.

5. The disposable absorbent article of claim 1 wherein said front and rear sections are each constructed of a sheet of a spunbond-meltblown-spunbond material and a sheet of a polyethylene secured together.

6. The disposable absorbent article of claim 5 wherein said sheets are secured together by a construction adhesive.

7. The disposable absorbent article of claim 1 additionally comprising fastening tapes for securing said first side edge of said front section to said first side edge of said rear section and for securing said second side edge of said front section to said second side edge of said rear section.

8. The disposable absorbent article of claim 7 wherein said fastening tapes are selected from the group consisting of adhesive tapes and multi-hook tapes.

9. The disposable absorbent article of claim 7 wherein said front and rear sections are each constructed of a cloth-like, non-woven material and wherein said front section includes at least one zone to which said fastening tapes can releasably adhere.

10. The disposable absorbent article of claim 9 wherein said at least one zone comprises a patch of BOPP (Bi-axially Orientated Polypropylene film) in the case of adhesive fastening tapes, and a patch of a multi-loop or plush material in the case of multi-hook fastening tapes.

11. The disposable absorbent article of claim 1 wherein said intermediate section comprises a moisture pervious cover-stock layer, a moisture barrier layer and an absorbent material core disposed therebetween.

12. The disposable absorbent article of claim 11 additionally comprising a fluid-acquisition layer interposed between said core and said cover-stock layer.

13. The disposable absorbent article of claim 11 wherein said moisture barrier layer comprises a polyethylene film or a poly-laminate material.

14. The disposable absorbent article of claim 11 wherein said moisture barrier layer comprises a polyethylene film or a poly-laminate material having a non-woven layer.

15. The disposable absorbent article of claim 11 wherein said cover-stock layer is formed of a non-woven material.

16. The disposable absorbent article of claim 15 wherein said non-waven material is spunbonded polypropylene.

17. disposable absorbent article arranged to be worn by a wearer to trap and collect waste, said article comprising front section, a rear section and an intermediate section, said front section being formed of a flexible generally planar panel having a top edge, a bottom edge, a first side edge and an opposed second side edge, said bottom edge of said front section being of a generally arcuate concave shape having a first concave shaped end portion and a second concave shaped end portion, said first concave shaped end portion merging with said first side edge of said front section, said second concave shaped end portion merging with said second side edge of said front section, said rear section being formed of a single, flexible generally planar panel having a top edge, a bottom edge, a first side edge and an opposed second side edge, said bottom edge of said rear section being of a generally arcuate convex shape having a first convex shaped end portion and a second convex shaped end portion, said first convex shaped end portion merging with said first side edge of said rear section, said second convex shaped end portion merging with said second side edge of said rear section, said bottom edge of said front section and said bottom edge of said rear section being complementary in shape to each other and being formed from a single sheet of material severed into two sections along a common line, whereupon one of said severed sections forms said front section, with said common line forming said bottom edge of said front section and the other of said severed sections forms said rear section, with said common line forming said bottom edge of said rear section, said intermediate section being an elongated member formed of a flexible material having a first side edge, a second side edge and an pair of end edges, one portion of said intermediate section adjacent one of said pair of end edges being fixedly secured to said front section intermediate said first and second side edges of said front section, a second portion of said intermediate section adjacent the other of said pair of end edges being fixedly secured to said rear section intermediate said first and second side edges of said rear section, said first side edge of said front section being arranged to be releasably secured to said first side edge of said rear section, said second side edge of said front section being arranged to be releasably secured to said second side edge of said rear section to mount said disposable absorbent article on the wearer and to form first and second leg openings, said first leg opening defining a high cut at said front section and comprising said first concave shaped end portion of said bottom edge of said front section, an adjacent portion of said first side edge of said intermediate section, and said first convex shaped end portion of said bottom edge of said rear section, said second leg opening defining a high cut at said front section comprising said second concave shaped end portion of said bottom edge of said front section, an adjacent portion of said second side edge of said intermediate section, and said second convex shaped end portion of said bottom edge of said rear section, said intermediate section being elasticized adjacent said first and second side edges thereof to conform to the crotch of the wearer, said intermediate section being arranged to absorb and trap waste material therein.

18. The disposable absorbent article of claim 17 additionally comprising fastening tapes for securing said first side edge of said front section to said first side edge of said rear section and for securing said second side edge of said front section to said second side edge of said rear section.

19. The disposable absorbent article of claim 17 wherein said front and rear sections are each constructed of a poly-laminate material comprising a layer of spunbond-meltblown-spunbond non-woven material and a layer of polyethylene film secured together.

20. The disposable absorbent article of claim 17 additionally comprising elongated elastic members extending along said first and second sides of said intermediate section, said elastic members being normally under tension to cause said intermediate section to assume a cup-like configuration having a pair of upstanding walls having an outer surface, said upstanding walls generally conforming to the crotch of the wearer.

21. The disposable absorbent article of claim 17 wherein said intermediate section comprises a moisture pervious cover-stock layer, a moisture barrier layer and an absorbent material core disposed therebetween.

22. The disposable absorbent article of claim 21 additionally comprising a fluid-acquisition layer interposed between said core and said cover-stock layer.

\* \* \* \* \*